(12) United States Patent
Febo et al.

(10) Patent No.: US 11,160,695 B2
(45) Date of Patent: Nov. 2, 2021

(54) DISPOSABLE ABSORBENT ARTICLE WITH UNITARY TOPSHEET AND UNITARY ABSORBENT ARTICLE

(71) Applicant: The Procter & Gamble Company, Cincinnati, OH (US)

(72) Inventors: Pietro Febo, S. Giovanni Teatino (IT); Luigi Marinelli, S. Giovanni Teatino (IT)

(73) Assignee: The Procter & Gamble Company, Cincinnati, OH (US)

(*) Notice: Subject to any disclaimer, the term of this patent is extended or adjusted under 35 U.S.C. 154(b) by 504 days.

(21) Appl. No.: 16/021,136

(22) Filed: Jun. 28, 2018

(65) Prior Publication Data

US 2018/0311082 A1 Nov. 1, 2018

Related U.S. Application Data

(63) Continuation of application No. 14/843,493, filed on Sep. 2, 2015, now Pat. No. 10,034,800, which is a (Continued)

(30) Foreign Application Priority Data

Apr. 24, 2002 (EP) .................................... 02009095

(51) Int. Cl.
*A61F 13/534* (2006.01)
*A61F 13/539* (2006.01)
(Continued)

(52) U.S. Cl.
CPC .......... *A61F 13/534* (2013.01); *A61F 13/537* (2013.01); *A61F 13/539* (2013.01);
(Continued)

(58) Field of Classification Search
CPC .. A61F 2013/15373; A61F 2013/15382; A61F 2013/53024; A61F 2013/530379;
(Continued)

(56) References Cited

U.S. PATENT DOCUMENTS 3,523,536 A 8/1970 Ruffo
3,929,135 A 12/1975 Thompson
(Continued)

FOREIGN PATENT DOCUMENTS

EP 0394812 A1 10/1990
EP 0 293 482 B1 7/1994
(Continued)

OTHER PUBLICATIONS

PCT International Search Report for CM2655 dated Sep. 18, 2003.

*Primary Examiner* — Susan S Su
(74) *Attorney, Agent, or Firm* — William E. Gallagher

(57) ABSTRACT

The present invention relates to disposable absorbent articles such as sanitary napkins, panty liners, baby diapers, adult incontinence articles and sweat pads. According to the present invention the absorbent article in the region designated for liquid deposition on its wearer facing surface has a single layer topsheet onto which liquid to be absorbed is provided during use of the article. The absorbent article includes a backsheet forming the liquid barrier surface and a unitary absorbent core between the topsheet and the backsheet. Importantly the unitary core provides improved liquid handling to the absorbent article and increases the masking, i.e. ability to hide stains due to absorbed liquid, of the article. This is particularly beneficial in the context of articles for absorption of liquids with high color intensity, such as menstrual liquid or urine of older adults.

16 Claims, 1 Drawing Sheet

Related U.S. Application Data continuation of application No. 14/528,244, filed on Oct. 30, 2014, now Pat. No. 9,138,360, which is a continuation of application No. 14/462,603, filed on Aug. 19, 2014, now Pat. No. 9,144,524, which is a continuation of application No. 13/893,986, filed on May 14, 2013, now Pat. No. 8,841,506, which is a continuation of application No. 10/412,846, filed on Apr. 10, 2003, now Pat. No. 8,461,412.

(51) Int. Cl.
    *A61F 13/537*     (2006.01)
    *A61F 13/53*     (2006.01)
    *A61F 13/535*     (2006.01)
    *A61L 15/28*     (2006.01)
    *A61F 13/47*     (2006.01)
    *A61F 13/49*     (2006.01)
    *A61F 13/56*     (2006.01)
    *A61F 13/62*     (2006.01)

(52) U.S. Cl.
CPC .. *A61F 13/53708* (2013.01); *A61F 13/53713* (2013.01); *A61F 13/53752* (2013.01); *A61F 13/47* (2013.01); *A61F 13/49* (2013.01); *A61F 13/53* (2013.01); *A61F 13/535* (2013.01); *A61F 13/5611* (2013.01); *A61F 13/622* (2013.01); *A61F 2013/530007* (2013.01); *A61F 2013/53024* (2013.01); *A61F 2013/530036* (2013.01); *A61F 2013/5395* (2013.01); *A61F 2013/530233* (2013.01); *A61F 2013/530386* (2013.01); *A61F 2013/530481* (2013.01); *A61F 2013/530547* (2013.01); *A61F 2013/53721* (2013.01); *A61F 2013/53908* (2013.01); *A61F 2013/53991* (2013.01); *A61L 15/28* (2013.01)

(58) Field of Classification Search
CPC ........ A61F 2013/530394; A61F 2013/530386; A61F 2013/5395; A61F 2013/53966; A61F 2013/53975; A61F 2013/53991; A61F 13/53991; A61F 13/5395; A61F 13/53966

See application file for complete search history.

(56) References Cited

U.S. PATENT DOCUMENTS

| | | | |
|---|---|---|---|
| 4,045,833 A | 9/1977 | Mesek et al. | |
| 4,151,240 A | 4/1979 | Lucas | |
| 4,319,868 A | 3/1982 | Riemersma et al. | |
| 4,324,426 A | 4/1982 | Michelson | |
| 4,343,314 A | 8/1982 | Sramek | |
| 4,591,523 A | 5/1986 | Thompson | |
| 4,609,518 A | 9/1986 | Curro | |
| 4,629,643 A | 12/1986 | Curro | |
| 4,637,819 A | 1/1987 | Ouellette | |
| 4,695,422 A | 9/1987 | Curro | |
| 4,988,344 A | 1/1991 | Reising et al. | |
| 5,271,987 A | 12/1993 | Iskra | |
| 5,334,177 A | 8/1994 | Cohen | |
| 5,460,622 A | 10/1995 | Dragoo et al. | |
| 5,591,510 A | 1/1997 | Junker | |
| 5,603,707 A | 2/1997 | Trombetta et al. | |
| 5,653,702 A | 8/1997 | Brohammer et al. | |
| 5,821,179 A | 10/1998 | Masaki et al. | |
| 5,855,572 A | 1/1999 | Schmidt | |
| 5,866,242 A | 2/1999 | Tan et al. | |
| 6,068,620 A | 5/2000 | Chmielewski | |
| 6,200,297 B1 * | 3/2001 | Boulanger | A61F 13/476 604/385.04 |
| 6,261,580 B1 | 7/2001 | Lehrter et al. | |
| 6,319,342 B1 | 11/2001 | Riddell | |
| 6,403,857 B1 * | 6/2002 | Gross | A61F 13/534 604/365 |
| 6,420,626 B1 | 7/2002 | Erspamer et al. | |
| 6,455,753 B1 | 9/2002 | Glaug | |
| 6,485,667 B1 | 11/2002 | Tan | |
| 6,673,981 B1 | 1/2004 | Stroembom | |
| 6,713,661 B1 * | 3/2004 | Arndt | A61F 13/15203 604/366 |
| 7,465,373 B2 | 12/2008 | Graef et al. | |
| 8,105,301 B2 | 1/2012 | Baer et al. | |
| 8,461,412 B2 | 6/2013 | Febo et al. | |
| 8,841,506 B2 | 9/2014 | Febo et al. | |
| 9,138,360 B1 | 9/2015 | Febo et al. | |
| 9,144,524 B2 | 9/2015 | Febo et al. | |
| 10,034,800 B2 | 7/2018 | Febo et al. | |
| 2002/0007169 A1 | 1/2002 | Graef et al. | |
| 2002/0022813 A1 * | 2/2002 | Bewick-Sonntag | A61F 13/8405 604/378 |
| 2006/0069367 A1 | 3/2006 | Waksmundzki et al. | |
| 2008/0132136 A1 | 6/2008 | Uematsu et al. | |
| 2009/0062760 A1 | 3/2009 | Wright et al. | |
| 2012/0191055 A1 | 7/2012 | Nozaki et al. | |
| 2017/0181898 A1 | 6/2017 | Varona et al. | |
| 2018/0001591 A1 | 1/2018 | Dutkiewicz et al. | |

FOREIGN PATENT DOCUMENTS

| | | |
|---|---|---|
| JP | 04 303445 A | 10/1992 |
| WO | WO 96/00548 A1 | 1/1996 |
| WO | WO 97/03118 A1 | 1/1997 |
| WO | WO 97/03795 A1 | 2/1997 |
| WO | WO 97/03818 A1 | 2/1997 |
| WO | WO 00/74620 A1 | 12/2000 |
| WO | 02066740 A1 | 8/2002 |

* cited by examiner

DISPOSABLE ABSORBENT ARTICLE WITH UNITARY TOPSHEET AND UNITARY ABSORBENT ARTICLE

CROSS REFERENCE TO RELATED APPLICATION

This application is a continuation of application Ser. No. 14/843,493, filed Sep. 2, 2015, which is a continuation of application Ser. No. 14/528,244, filed Oct. 30, 2014 (now U.S. Pat. No. 9,138,360), which is a continuation of application Ser. No. 14/462,603, filed Aug. 19, 2014 (now U.S. Pat. No. 9,144,524), which is a continuation of application Ser. No. 13/893,986, filed May 14, 2013 (now U.S. Pat. No. 8,841,506), which is a continuation of application Ser. No. 10/412,846, filed Apr. 10, 2003 (now U.S. Pat. No. 8,461,412), which claims priority to EP Application No. 02009095.7, filed Apr. 24, 20002 (now EP Patent 1,356,797).

FIELD OF THE INVENTION

The present invention relates to disposable absorbent articles such as sanitary napkins, panty liners, baby diapers, adult incontinence articles and sweat pads. According to the present invention the absorbent article in the region designated for liquid deposition on its wearer facing surface has a single layer topsheet onto which liquid to be absorbed is provided during use of the article. The absorbent article further comprises a backsheet forming the liquid barrier surface and a unitary absorbent core between the topsheet and the backsheet. Importantly the unitary core provides improved liquid handling to the absorbent article and increases the masking, i.e. ability to hide stains due to absorbed liquid, of the article. This is particularly beneficial in the context of articles for absorption of liquids with high color intensity, such as menstrual liquid or urine of older adults.

BACKGROUND OF THE INVENTION

Absorbent articles are well known in the art. Particularly sanitary napkins of all kinds of designs are well documented. Although the use of unitary cores is known in the art of disposable absorbent articles and has been disclosed previously such articles have not been successful or technically satisfactory as evidenced by the lack of commercially available embodiments.

The word "unitary" as used herein refers to a single structure, which despite potential internal variations of physical and/or chemical characteristics is provided such that it cannot be separated into individual layers. Such unitary structures are well known in the art and often referred to also as substrates. However, absorbent cores in disposable absorbent articles have been provided from a number of layers or associated with a multi-layer structure as the topsheet. In this context it is pointed out that a construction in which a topsheet with a second underlying layer, (at least in the region where liquid is usually deposited onto the article), referred to as secondary topsheet or distribution layer, is provided on top of a unitary absorbent structure, is excluded from the definition of the absorbent articles according to the present invention. Also structures made from a number of layers, which are joined to each other by macroscopic mechanical or adhesive means, are well know and not uncommon in the practical embodiments of absorbent articles available to consumers. Such structures, however, are also not considered unitary in the sense of the present invention since they are formed from individual layers that, albeit sometimes with difficulty, can be separated from each other again.

A unitary fluid acquisition, storage and wicking material is disclosed for example in WO 0074620 in which fibrous absorbent structures having separate strata or thickness regions for fluid acquisition storage and distribution are disclosed.

This disclosure, however, suffers from the design of an acquisition, storage and distribution layer system, which simply resembles the designs obtainable by a combination of layers. The fact that these layers are laid down in a single process, preferably as an air laid process, does not change the deficiencies originally found in the multi-layered constructions widely used in commercial article with the exception that the liquid communication between the layers is improved. The present application, however, also improves the ability of such unitary structures to mask stains visible on the topsheet side of an absorbent article, besides providing excellent liquid communication characteristics between the differing layers or strata.

The present invention also is particularly directed to the absorbent article employing unitary absorbent cores in such a way that no additional layers between the unitary topsheet and the unitary absorbent core is provided at least in the region where liquid is deposited during usual use. It is therefore an advantage of the present invention that a lay down of three layers, a topsheet, a unitary absorbent core and a backsheet is capable of providing the full and improved functionality of absorbent articles and thereby reduces manufacturing complexity for such articles. Within the various aspects of manufacturing complexity it should be noted that the simplification in raw material procurement, raw material delivery to a production facility and simplification of combining the raw materials to a finished absorbent article is much simplified with the absorbent article design according to the present invention.

SUMMARY OF THE INVENTION

According to the present invention a disposable absorbent article such as a sanitary napkin having a wearer facing surface and a garment facing surface is provided which article comprises a topsheet, a backsheet (preferably joined to the topsheet), and an absorbent core interposed between the topsheet and the backsheet. Each of the components, topsheet, backsheet, and absorbent core, has a wearer-facing surface and a garment-facing surface.

The disposable absorbent article has a liquid deposition region in which during conventional use of the article, liquids are deposited for absorption in the article.

The topsheet forms the outermost surface and the wearer-facing surface of the absorbent article. The liquid pervious topsheet consists of a single layer at least in the liquid deposition region. The backsheet forms the liquid barrier surface and the garment-facing surface of the article. The absorbent core is intermediate the topsheet and the backsheet. The absorbent core is unitary and has a wearer facing and a garment-facing surface. The garment-facing surface of the core is immediately adjacent, (that is in direct liquid contact with) the backsheet and the wearer-facing surface of the absorbent core is immediately adjacent to the topsheet.

The unitary core is provided as a fibrous stratified layer structure with at least three layers. All layers are unified into a unitary core by a single thermal combining step or by a single felting step or by a combination of both a thermal combining and a felting step. There is no adhesive used between the layers of the absorbent core, as this is not necessary due to the unitary construction and the combining being conducted on the layers in a single step.

The at least three layers of the absorbent core comprise a first outermost layer forming the wearer-facing surface of a core. The first layer is provided as a mixture of bi-component fibers and cellulose or viscose fibers, but preferably non-softened cellulose fibers that together provide an overall weight fraction of the absorbent core or 10%-30%. The core has a second outermost layer, which forms the garment-facing surface of the core. The second layer of the core is provided by softener treated cellulose fibers. This layer of the core provides an overall weight fraction of a core of 30%-50% and optionally comprises a surface binder, preferably latex, as a dust control means, which is applied onto the garment-facing surface of the core in an amount of 0%-2% by weight of the core.

Finally, the absorbent core has at least one inner layer, which is sandwiched between the first and the second layer. This inner layer comprises non-softened cellulose fibers, optionally a bi-component fiber, preferably mixed homogeneously with the non-softened cellulose fibers. The inner layer further comprises a super-absorbent material, preferably in particulate form. The inner layer has a weight fraction of the overall core between 30% and 50% of the core. The disposable absorbent article is particularly characterized in that the unitary core is free of binder material, except for the bi-component fibers in the layers of the core and the optional surface binder on the garment-facing surface of the core.

In a preferred embodiment the surface binder for dust control is not required in the absorbent core. In a further preferred embodiment according to the present invention, the first layer of the absorbent core comprises between 60% and 95% by weight of the bi-component fibers and 5% -40% by weight of cellulose or viscose fibers. Preferably the bi-component fibers have a cross section with a polypropylene central portion and a polyethylene outer coating around the polypropylene. More preferable and resulting in a curled bi-component fiber is if the polypropylene central portion is not symmetrical in respect to the center point of the cross section of the bi-component fibers. This results in curling of the bi-component fibers providing extra resiliency at least to the first layer of the absorbent core.

In a yet alternative preferred embodiment the bi-component fibers of the inner layer of the absorbent core has a large diameter by having a coarseness of at least 10 dtex, preferably between 12 dtex and 20 dtex and more preferably between 15 dtex and 18 dtex. Finally, for ease of manufacturing and without sacrifice of performance of the absorbent article according to the present invention, a highly preferred embodiment will use only one kind of bi-component fibers in accordance with the above-preferred designs.

DETAILED DESCRIPTION OF THE INVENTION

Figure 1:
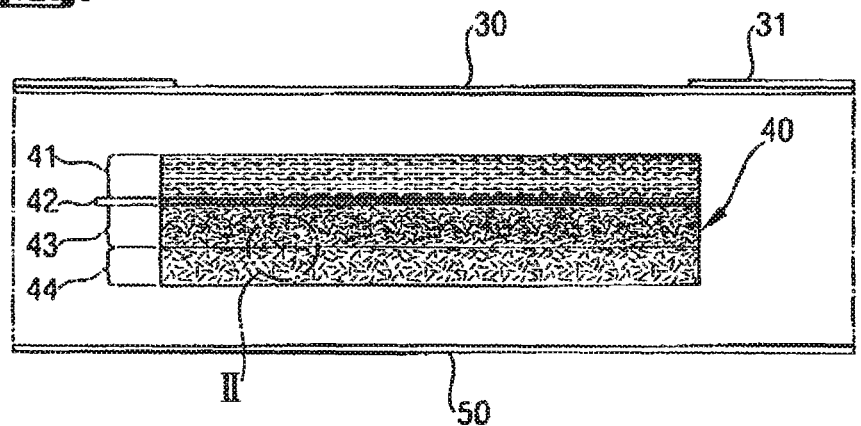
FIG. 1 shows a schematic cross section of a sanitary napkin showing the internal layered structure of a sanitary napkin according to a preferred embodiment of the present invention.

The present invention relates to absorbent disposable articles such as sanitary napkins, panty liners, incontinence product, sweat pads, and baby diapers. Typically such products comprise the elements of a liquid pervious topsheet, a backsheet and an absorbent core intermediate said topsheet and said backsheet. According to the present invention, the topsheet, backsheet, and core may be selected from any of the known types of these components provided that they meet the design and material criteria and conditions noted below and in the appended claims.

In general, the topsheet should have good liquid retention to maintain a dry surface and thereby keep the skin of the wearer dry; the absorbent core needs to provide enough absorbent capacity and preferably allows the flow of vapor and/or air through it and the backsheet should prevent wet through (liquid impermeability) to retain the absorbed fluid while preferably being sufficiently breathable. Furthermore, the individual elements are joined to each other, preferably using techniques such that the final product has the desired comfort and performance level.

In the following description of the invention the surface facing in the direction of the wearer is called wearer-facing surface. In the drawing this direction is towards the top of the page. Further the surface facing in the direction of the garment is called a garment-facing surface and in the drawing this direction is towards the bottom of the page.

In the following description the term "a liquid deposition region" of the article is used. The liquid deposition region is that region of the article where in usual use liquid is predominantly deposited. The region hence depends in its exact dimension and location on the article. The skilled person will however know or be able to define the minimum dimension and location of the liquid deposition region. In particular for feminine care articles, i.e. napkins or panty liners, this region is centrally located having a 2-5 cm minimum width and 3-12 cm minimum length.

Absorbent Article Components

The Topsheet

According to the present invention the absorbent article comprises a liquid pervious topsheet. The topsheet suitable for use herein comprise wovens, non-wovens, and three-dimensional webs of a liquid impermeable polymeric film comprising liquid permeable apertures. In FIG. 1 the topsheet is indicated with reference numeral 30.

The topsheet for use herein is a single layer at least in the liquid deposition region but may have a multiplicity of layers (31) outside of the liquid deposition region. In a preferred embodiment the topsheet across its full extension is a single layer, which provides the user-facing surface of the topsheet in the liquid deposition region and the garment-facing surface of the topsheet. Optionally on the wearer facing surface of the topsheet but only extending in the peripheral zone of the article an additional layer can be desirable to provide extra softness or extra liquid handling/retaining abilities (this design is usually referred to as "hybrid topsheet"). The topsheet typically extends across the whole of the absorbent structure and can extend into and form part of or all of the preferred but optional side flaps, side-wrapping elements, wings or ears. Also the topsheet can wrap around the absorbent core edges. Fundamentally the topsheet can be provided as a single layer, which for simplicity of manufacturing is the preferred design.

The topsheet as a whole needs to be compliant, soft feeling, and non-irritating to the wearer's skin. It also can have elastic characteristics allowing it to be stretched in one or two directions. The topsheet has the principle function of acquisition and transport of fluid from the wearer towards the absorbent core and containment of the absorbent core. In addition to liquid permeability the topsheet should have a high vapor permeability and/or air permeability.

According to the present invention the topsheet can comprise woven, non-wovens, but preferably a liquid permeable apertured polymeric film, preferably the wearer facing and contacting surface at least in the liquid deposition region, is provided by a film material having apertures which are provided to facilitate liquid transport from the wearer facing surface towards the absorbent structure. Such liquid permeable, apertured films are well known in the art. They provide a resilient three-dimensional fiber-like structure. Such films have been disclosed in detail for example in U.S. Pat. No. 3,929,135, U.S. Pat. No. 4,151,240, U.S. Pat. No. 4,319,868, U.S. Pat. No. 4,324,426, U.S. Pat. No. 4,343,314, U.S. Pat. No. 4,591,523, U.S. Pat. No. 4,609,518, U.S. Pat. No. 4,629,643, U.S. Pat. No. 4,695,422 or WO 96/00548.

An example of such film is available from the Procter & Gamble Company, Cincinnati, Ohio, USA under the trade name Dry weave. Also such films are available from the Company Pantex from Pistoia, Italy under the designation "PF-films". Also film according to U.S. Pat. No. 5,591,510 or WO 97/03118 and WO 97/03795 described for use as a layer in breathable backsheet can be employed but may require modification of the apertures to ensure liquid permeability from the wearer-facing surface to the absorbent core that is the primary objective of the topsheet. Such modification can e.g. be a surface energy alteration that actively drives liquids into and through apertures by creating a gradient of surface tension of the film. A method to provide surface energy gradients is disclosed e.g. in WO 96/00548.

Absorbent Core

According to the present invention, the absorbent cores suitable for use herein are unitary. In FIG. 1 the absorbent core is shown as a single layer 40 constituted by sub-layers or strata 41, 42, 43, 44.

The absorbent core of the present invention should have high vapor permeability preferably also high air permeability. The absorbent core preferably has a caliper or thickness of less than 12 mm, preferably less than 8 mm, more preferably less than 5 mm, most preferably from 4 mm to 2 mm.

According to the present invention, the absorbent core includes the following sub-layers: (a) a first outermost layer 41 providing the surface adjacent the topsheet 30 optionally together with an intermediate layer 42; (b) a fluid storage layer 43; (c) a second outermost layer 44 providing the surface adjacent the backsheet.

First Layer

One component of the absorbent core according to the present invention is a first layer. The first layer underlies the topsheet and is in direct fluid communication therewith. The topsheet transfers the acquired fluid to this first layer for ultimate distribution to the storage layer. This transfer of fluid through the primary distribution layer occurs primarily but not only in the thickness, but also along the length and width directions of the absorbent product.

The first layer forms the wearer-facing surface of the absorbent core and is hence a layer of an outermost surface of the core. The first layer is provided from mixtures of fibers. The mixture of fibers consists of bi-component fibers and hydrophobic fibers as celluloses and/or viscose fibers, preferably non-softened cellulose fibers. Preferably the mixture is selected such that 60%-95% by weight of the first layer is provided by bi-component fibers and 5%-40% by weight is provided by cellulose and/or viscose fibers. Of course, a mixture of (non-treated) cellulose and viscose fibers may also be chosen, as these are considered equivalent. In a preferred embodiment the amounts will be even stricter selected to be 80%-90% by weight of the bi-component fibers and 10%-20% by weight of (non-treated) cellulose or viscose fibers.

As used hereinafter the term bi-component fibers refers to fibers having two constituents. Typically bi-component fibers are constituted of relatively similar constituents, which are differing, for example in their melting temperature or softening temperature. Particular embodiments and preferred in the context of the present invention are polypropylene/polyethylene bi-component fibers but other combinations such as polyester/polyethylene, polyester/polypropylene, polyamide/polyester, polyamide/polyethylene, polyamide/polypropylene are also feasible combinations. The conventionally used material is, however, the above-mentioned polypropylene polyethylene fiber composition which is provided in a form such that in a cross-sectional view of a fiber the material with the higher melting or softening point provides the central part or the core of the fiber and typically is responsible for the fiber ability to transmit forces and have a certain rigidity or provide structures with resiliency while the outer coating on the core of the fiber has a lower melting point and is used to facilitate thermally bonding of substrates comprising such fibers. It is particularly preferred if the so-called shaft core design of bi-component fibers is not exactly point-symmetrical to the central point of the cross section but provides the shaft part of the fiber in an asymmetric form so that the fiber is caused to curl. This has been found to provide a beneficial effect on resiliency and strength of the fiber.

In a typical embodiment according to the present invention, a polypropylene core is provided with a polyethylene coating on the outside in an asymmetric form such that in a highly preferred embodiment, in about 50% of the fiber material is polypropylene and 50% of the fiber material is polyethylene. Other quantitative amounts can of course be selected and will strongly depend on the overall fiber dimensions as the binder quantity of the surface of the fiber provided preferably by the polyethylene needs to have a certain thickness in absolute terms for the provision of good bonding while its relative quantity can vary. According to the present invention very thick fibers can be used and it has been found that bi-component fibers of the polyethylene polypropylene kind, but also other material compositions as indicated above, are preferably provided in a coarseness of at least 10 dtex, preferably between 12 dtex and 20 dtex and more preferably between 15 dtex and 18 dtex. An example of such bi-component fibers is available from the company ES Fibervision, Engdraget 22, DK-6800 Varde, Denmark, under the trade name ES-Delta having 16.7 dtex and being provided by a polypropylene core and fully coated by polyethylene. These fibers are available in carded form, having a length of approximately 4.6 mm, which have been found useful in the context of the present invention. An example of fine bi-component fibers, usable in the present invention especially in the first layer are Al Adhesion 1.7 dtex also from the company Fibervsion.

The other fiber used in the context of the present invention in the first layer is the fiber of (non-treated) cellulose or viscose/rayon fibers or combinations thereof. The term "treated" in this context typically refers to softening treatment and both terms are used synonymously herein. Such fibers are widely available and are made in the context of manufacturing of paper. These fibers historically have been well-known and both versions, the more brittle and less flexible non-softened cellulose fibers, which have simply not undergone a treatment with a softening material, such as for example a quaternary ammonium material, well-known in the art of paper making, are used in the layer to reinforce this particular resiliency desirable for this first layer. This provides exceptional capability of allowing liquid to be acquired without collapsing under its own weight. Particularly preferred and used in an embodiment according to the present invention is the use of viscose/rayon fibers in this first layer at an amount of about 15%. Such viscose/rayon fibers are available from a large number of commercial sources. The remainder of the first layer structure was provided by the above-mentioned fibers provided by Fibervision (Supra).

As can be seen from the drawing FIG. 1, the first layer 41 is followed by a second layer (42) indicated by small dots implying that this is a particularly thin layer of purely bi-component fibers or low melting point thermoplastic fibers such as polyethylene fibers, providing especially good thermo integration with the following layer (43).

In a separate consideration, this layer could also be provided by an extremely fine mix of adhesive fibers that are sprayed in the course of manufacturing of the unitary core according to the present invention. As the present invention as defined in the claims does not include such design due to the use of adhesive, it is here only mentioned as a potential alternative, which, in case of search for an alternative to the present invention, could be useful with minor sacrifice of some of the beneficial characteristics of the present invention. It is even conceivable to combine the first layer with the remainder of the unitary core structure by such a mix of adhesive fibers after having integrated i.e. bonded the first layer and/or the remainder of the unitary core layers prior to this binding. This not being preferred in accordance with the present invention as claimed, nevertheless it is a possibility that for the sake of completeness should be mentioned in this context.

However, for the particularly beneficial embodiments according to the present invention, which in accordance with claim 1 as filed do not require any adhesive material layer (42) could also be provided by thermoplastic particles such as polyethylene powder. One preferred embodiment according to the present invention will simply not have a layer (42) in order to limit the structure to its most simple form (thereby simplifying the manufacturing process of the unitary core) to a three-layer structure.

Fluid Storage Layer

Positioned in fluid communication with, and typically underlying the first layer, is a fluid storage layer (43). The fluid storage layer comprises absorbent gelling materials usually referred to as "hydro gel", "super-absorbent", hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier but is preferably dispersed homogeneously.

Suitable absorbent gelling materials for use herein will most often comprise particles of a substantially water-insoluble, slightly cross-linked, partially neutralized, polymeric gelling material. This material forms a hydro gel upon contact with water such polymer materials can be prepared from polymerizable, unsaturated, acid-containing monomers, which are well known in the art.

Suitable carriers include materials, which are conventionally utilized in absorbent structures such as natural, modified or synthetic fibers, particularly non-softened cellulose fibers (in the form or fluff) or combination thereof. However especially non-treated cellulose available e.g. from the Weyerhauser company are used in the fluid storage layer according to the present invention.

A small amount of less than 50% weight of synthetic fibers can in addition also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bi-component fibers, tricomponent fibers, fibers with surface capillaries, mixtures thereof and the like. Preferably, the fiber surfaces of such fibers are hydrophilic or are treated to be hydrophilic. The storage layer can also include filler materials, such as Perlite, diatomaceous earth, Vermiculite, etc., to improve liquid retention. Preferred is the use of a minor amount of bi-component fibers of the same kind used in the first layer.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution preferably is used to leave portions of the entire periphery of the fluid storage layer free of absorbent gelling material or at least with reduced amounts.

In an example of the fluid storage layer according to the present invention a mixture of 30% by weight of the layer is absorbent gelling material, 60% by weight of the layer is provided by non-softened cellulose fibers and 10% are bi-component fibers of the same kind used in the first layer.

Second Layer

The second outermost layer for inclusion in the absorbent core according to the present invention is a fibrous layer 44 adjacent to, and typically underlying the storage layer. This underlying fibrous layer or second outermost layer forms the garment-facing surface of the absorbent unitary core. The second layers provided by softener treated cellulose fibers providing this cellulose with a particularly good wetting surface and a reduced resiliency, thereby creating a denser cushioning effect in that layer of the absorbent structure farthest away from the wearer during use of the article. This layer should provide 30-50% of the overall weight of the absorbent structure and should be provided exclusively by softener treated cellulose fibers or viscose fibers or a combination thereof. It is, however, due to the large amount of short fibers found in such softener treated cellulose fluff materials possible to provide the outermost surface, i.e. the garment facing surface of this layer with a minor amount of binder material sprayed or otherwise distributed onto the outermost surface of this layer. This binder material is not intended nor does it support binding of the overall absorbent core but only provides a reduced dustiness and broken fiber departure from the surface of the second layer. In particular this may only be a manufacturing process related application of binder material for dust control rather than intended to affect the absorbent core performance aspects. The amount of such binder can be between 0% and 2%, preferably between 1% and 0% by weight of the absorbent core and of course preferably left away if the dust control can be achieved by different means during manufacturing of such articles. Binders can be e.g. latex type binders but simply using water has also been found possible.

Other Optional Components of the Absorbent Structure

The absorbent core according to the present invention can include other optional components normally present in absorbent webs. For example close to or as part of the first layer or the fluid storage layer odor control agents such as zeolites, carbon black, silicates, EDTA or other gelatins can be provided. Such agents are preferably provided in particulate form or as part of particles and can be provided for example together with the absorbent gelling material mentioned supra.

Integration of Layers in Unitary Core

According to the present invention, the unitary core is provided as a single unitary structure. Thermo bonding or felting or combinations of these combining steps create it. Hence, the unitary core before any bonding can take place, needs to be provided by laying the various materials described above onto each other, then a calendaring will take place in order to reduce the thickness and bulkiness of the structure. The calendaring step creates a densification, which provides the same force throughout the whole of the structure. This calendaring is then followed by the thermo bonding or felting with needles or a combination such as felting with hot needles and a hot air exposure of the unitary absorbent core structure.

It should be particularly noted that calendaring needs not be provided in a single step, it could be provided in two or more steps. However importantly the calendaring is conducted on the unitary structure as a whole, not on the individual layers.

Before the bonding between the layers, there is no particular integrity within and between the layers of the core such that forces within the absorbent structure are not supportable by the absorbent structure prior to bonding. Hence, the calendaring needs to take place very carefully and will create already a minor mechanical integration between the various layers.

Interestingly it has been found that provided the above-mentioned design criteria are followed, the compression will result in a higher densification of the second outermost layer while the first outermost layer, due to the high amount of bi-component fibers and their resiliency will relatively expand more than the second outermost layer, thereby creating a density gradient from the wearer facing surface towards the garment facing surface of the absorbent structure. This gradient coincides with the same kind of gradient for capillarity which is having the largest capillaries in the first layer, followed reducing capillaries towards the second layer throughout the thickness of the absorbent core. Both, the capillary as well as the density gradient are particularly beneficial for the absorbent performance as liquid is driven into the material and not released from it, but stored in the storage core. This also has the surprising effect of providing an unsurpassed masking effect for the absorbent structure in that liquids, such as menstrual fluid or urine of older people having a rather strong yellowish color, will penetrate into the structure but be distributed within the structure, thereby displaying on the outer surface a reduced visibly detectable stain size for the same kind of deposition when compared with conventional structures or even the same combination of layers but adhesively attached to each other.

Figure 2:
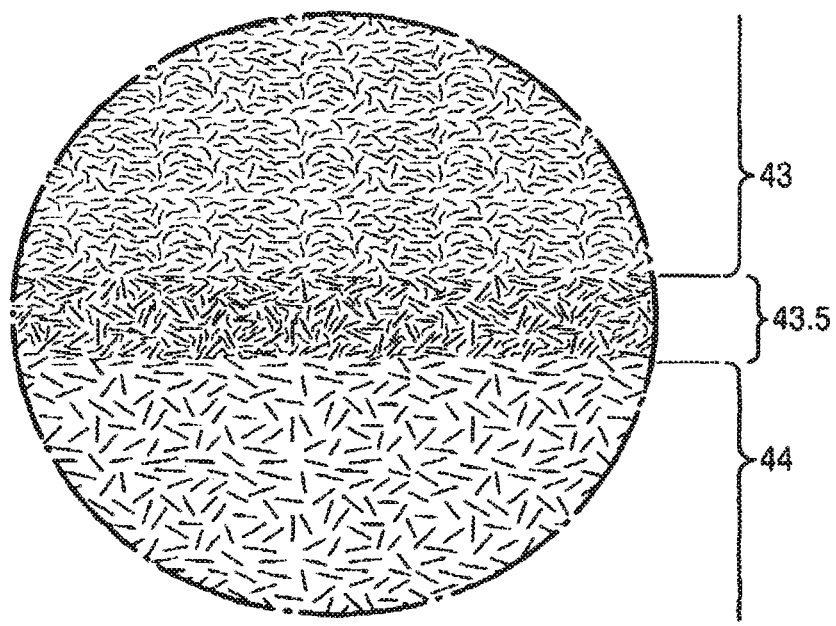
FIG. 2 shows an enlarged portion II of the absorbent structure of the napkin of FIG. 1 including a schematic view of the transition between two layers in the core.

As can be seen in FIG. 2, the region between one layer, in this Figure exemplified as layer (43) and a second layer, in this Figure simplified as layer (44), is a non-discreet transition zone (43.5). In this transition zone, the materials from one layer have mixed with materials from the adjacent layer. When combining the absorbent core in accordance with the present invention, these transition zones, albeit extremely thin relative to the other layers, create an even stronger integration between the layers of the absorbent core according to the present invention. Once integrated, the absorbent core structure cannot be separated without destruction of this transition zone formed by the integration of the absorbent core. Hence, when attempting to evaluate cores for compliance with the requirements of the present invention, it is necessary to use statistical means of separations in order to find reasonably accurate measurements of the quantities of materials in the various layers. One way of facilitating separation of layers in the absorbent core according to the present invention is to use methods of deep-freezing, such as exposure to liquid nitrogen and cutting of the layers under a microscope while the layers are in their frozen state. Such cuts have to be made in the center of the transition zones (43.5) as shown in FIG. 2.

The transition zones are technically important as they prevent step changes in characteristics such as capillarity, density, material-composition (due to material mixing). They are a result of the unitary formation of the cores. Many variations in the embodiments according to the present invention are possible and are only limited by the scope of the appended claims.

Backsheet

The absorbent article according to the present invention also comprises a backsheet (50). The backsheet primarily has to prevent the extrudes absorbed and contained in the absorbent structure from wetting materials that contact the absorbent article such as underpants, pants, pajamas, undergarments, and shirts or jackets, thereby acting as a barrier to fluid transport. In addition, however, the backsheet according to a preferred embodiment of the present invention permits the transfer of at least water vapor, preferably both water vapor and air through it and thus allows the circulation of air into and water vapor out of the article. The backsheet typically extends across the whole of the absorbent structure and can extend into and form part or all of side flaps, side wrapping elements or wings, if present.

For a preferred embodiment according to the present invention suitable breathable backsheet for use herein comprise at least one impervious polymeric backsheet layer such as a polyethylene film. The backsheet can alternatively comprise a resilient three-dimensional web, which consists of a liquid impermeable film which has valve like apertures and is air/vapor permeable while retarding liquid transport. Preferred breathable backsheet for use herein are those having a high vapor exchange, most preferably both a high vapor and high air exchange. The film is oriented such that it retards or prevents liquid from passing from the absorbent core towards the outside due to the valve like apertures while allowing free airflow through it.

In another embodiment an additional backsheet layer is provided together with the above-mentioned aperture film. The additional layer is at least water vapor permeable so as to support breathability of the article. It is not required but desirable that it also supports air permeability in order to further improve the comfort benefit from the breathability of the article. In this context suitable water vapor and air permeable layers include two-dimensional micro- or macro-aperture films, which can also be micro- or macroscopically expended films, formed aperture films and monolithic films, as well as nonwovens, or wovens. Such films are disclosed in detail e.g. in EPO 293 482 and the references therein, or U.S. Pat. No. 3,929,135, U.S. Pat. No. 4,637,819 and U.S. Pat. No. 4,591,523. Preferably this film layer is made in accordance with the aforementioned U.S. Pat. No. 5,591,510 or PCT WO-97/03818, WO-97/03795. In particular, this layer comprises a polymeric film having capillaries. The preferred capillaries extend away from the wearer facing surface of film at an angle that is less then 90 degrees. For ease of manufacturing a single layer or a recombined multi layer structure for use as backsheet 50 is desirable.

Absorbent Article Construction

According to the present invention the elements of the article, the topsheet, backsheet and absorbent core elements, are joined to each other. The elements or layers are joined together across all or parts or portions of their common interface. In this manner the topsheet is joined to the absorbent core, and the core is joined to the backsheet. Furthermore, if the backsheet comprises more than one layer, these layers may also be similarly joined. In a particularly preferred embodiment the topsheet and backsheet extend beyond the periphery of the absorbent core and the topsheet is directly (or indirectly) joined to the backsheet to contain the absorbent core. In this context indirectly joining includes joining by means of an intermediate layer such as a layer of adhesive or another layer while direct joining includes adhesive joining by a distributed adhesive network or other means creating direct contact between layers, which are joined.

The elements of the article may be joined by any means known in the art for affixing two adjacent layers of material, such that the layers are directly attached to one another or directly attached to one another via the joining means. Suitable joining means include adhesive, fusion bonding, ultra sonic bonding, stitching, heat (e.g. thermo bonding by welding fibers at intersections or melting a polymer to attach fibers or films to each other), embossing, crimping, pressure bonds, dynamic mechanical bonds or combinations thereof.

Especially if the absorbent article finds utility as a sanitary napkin or panty liner, the absorbent article is also provided with a panty fastening means, which provides means to attach the article to an undergarment. For example the panty fastening means may comprise a mechanical fastener such as hook and loop fasteners such as marketed under the trade name VELCRO, snaps or holders. Alternatively, the article is fastened to the undergarment by means of panty fastening adhesive on the backsheet. The panty fastening adhesive provides a means for securing the article to the panty and preferably a means for securing the article when soiled, to a fold and wrap package for convenient disposal.

According to the present invention the absorbent article can be used beneficially in the context of sanitary napkins, panty liners, incontinence articles, sweat pads and diapers. However, sanitary napkins and panty liners are particularly susceptible to the present invention. The disposable article may thus also have all those features and parts, which are typical for products in the context of their intended use. For sanitary napkins this includes particularly wings or side flaps which are provided on the side edges of the napkin and which fold around the crotch edge of an undergarment. The side flaps can be provided as extensions of one or several of the elements of the napkin such as the topsheet and/or backsheet. They can also be made separately and be joined to the side margin of the napkin.

What is claimed is:

1. A disposable absorbent article, comprising:
a liquid pervious topsheet;
a backsheet;
an absorbent core disposed between the liquid pervious topsheet and the backsheet; and
wherein the absorbent core comprises an outer wearer facing surface and an opposing outer garment facing surface, and a first layer that forms at least a portion of the wearer facing surface, a fluid storage layer in fluid communication with the first layer, and a second layer in fluid communication with the fluid storage layer, wherein the first layer comprises a plurality of bi-component fibers and a plurality of viscose fibers, wherein a ratio of bi-component fibers to viscose fibers in the first layer ranges from 19:1 to 3:2, and wherein the absorbent core has a caliper of between about 2 mm and about 12 mm.

2. The absorbent article of claim 1, wherein the topsheet is joined to the first layer of the absorbent core via fusion bonding or ultrasonic bonding.

3. The absorbent article of claim 1, wherein the topsheet is joined to the first layer of the absorbent core via stitching, crimping, or dynamic mechanical bonding.

4. The absorbent article of claim 1, wherein the bi-component fibers are asymmetrical.

5. The absorbent article of claim 1, wherein the ratio of bi-component fibers to viscose fibers is from about 9:1 to about 4:1.

6. The disposable absorbent article of claim 5, wherein the fluid storage layer comprises superabsorbent material.

7. The disposable absorbent article of claim 6, wherein the second layer comprises a plurality of nonwoven fibers.

8. The disposable absorbent article of claim 7, wherein the plurality of nonwoven fibers comprise cellulose.

9. The disposable absorbent article of claim 8, wherein a first transition zone is disposed between the first layer and the fluid storage layer.

10. The disposable absorbent article of claim 9, wherein a second transition zone is disposed between the second layer and the fluid storage layer.

11. The disposable absorbent article of claim 8, wherein a second transition zone is disposed between the second layer and the fluid storage layer.

12. The disposable absorbent article of claim 7, wherein the fluid storage layer and the second layer are integrated via calendaring.

13. The disposable absorbent article of claim 7, wherein the second layer has a higher density than the first layer.

14. The absorbent article of claim 1, wherein the bi-component fibers comprise a dtex of from about 10 to about 20.

15. The absorbent article of claim 1, wherein the bi-component fibers comprise a dtex of from about 12 to about 20.

16. The absorbent article of claim 1, wherein the bi-component fibers comprise a dtex of from about 15 to about 18.

* * * * *